ations"

United States Patent [19]
Carrier et al.

[11] Patent Number: 5,654,198
[45] Date of Patent: Aug. 5, 1997

[54] DETECTABLE WATER-TREATMENT POLYMERS AND METHODS FOR MONITORING THE CONCENTRATION THEREOF

[75] Inventors: Allen M. Carrier, Hixson, Tenn.; Robert W. R. Humphreys, Annandale; Paul M. Petersen, Three Bridges, both of N.J.

[73] Assignee: National Starch and Chemical Investment Holding Corporation, Wilmington, Del.

[21] Appl. No.: 462,244

[22] Filed: Jun. 5, 1995

[51] Int. Cl.⁶ ................................................. G01N 21/29
[52] U.S. Cl. .................... 436/6; 436/164; 436/93; 436/94; 526/238.2; 526/238.23
[58] Field of Search ................... 436/164, 85, 805, 436/93, 94, 6; 526/238.2, 238.23

[56] References Cited

U.S. PATENT DOCUMENTS

| | | | |
|---|---|---|---|
| 2,891,944 | 6/1959 | Boettner | 260/211 |
| 3,992,149 | 11/1976 | Wang | 436/164 |
| 4,451,628 | 5/1984 | Dammann | 536/225 |
| 4,504,643 | 3/1985 | Boutin et al. | 526/287 |
| 4,514,504 | 4/1985 | Rothman | 436/85 |
| 4,709,091 | 11/1987 | Fukumoto et al. | 562/595 |
| 4,711,725 | 12/1987 | Amick et al. | 210/701 |
| 4,721,760 | 1/1988 | Graafland | 526/238.23 |
| 4,783,314 | 11/1988 | Hoots et al. | 422/3 |
| 4,843,154 | 6/1989 | Klein et al. | 536/4.1 |
| 4,892,898 | 1/1990 | Leighton et al. | 524/3 |
| 5,032,526 | 7/1991 | Myers et al. | 436/85 |
| 5,171,450 | 12/1992 | Hoots | 210/701 |
| 5,194,639 | 3/1993 | Connor et al. | 554/66 |
| 5,238,846 | 8/1993 | Aucutt | 436/38 |

FOREIGN PATENT DOCUMENTS

| | | |
|---|---|---|
| 0 613 863 A1 | 1/1994 | European Pat. Off. . |
| 0 220 676 A1 | 10/1986 | Germany . |
| 0 383 023 A2 | 1/1990 | Germany . |
| WO 92/06984 | 4/1992 | WIPO . |
| WO 92/08687 | 5/1992 | WIPO . |

OTHER PUBLICATIONS

Electro–Optics Handbook, RCA, Tech. Ser. EOH–11, 1974, pp. 14, 56, 57.
Joachim Klein, "New Surfactant Polymers Based on Carbohydrates", Makromol. Chem. 191, 517–528 (1990).

Primary Examiner—Mark Nagumo
Attorney, Agent, or Firm—William K. Wissing

[57] ABSTRACT

Water-treatment compositions are provided which contain a water-soluble, water-treatment polymer and, optionally, additional water-treatment chemicals. The polymers are prepared from water-treatment monomers and a photo-inert, latently-detectable moiety which is covalently bonded to the polymer backbone. When the residue of the photo-inert moiety is contacted with an amount of a photoactivator which is effective to cause the residue of the photo-inert moiety to absorb within a wavelength ranging from 300 to 800 nanometers, the residue of the photo-inert moiety is detectable at concentrations of less than 100 parts per million. Methods are also provided which allow for the determination of the concentration of low levels, i.e., less than 100 ppm, of the water-treatment polymer present in an aqueous system.

6 Claims, No Drawings

DETECTABLE WATER-TREATMENT POLYMERS AND METHODS FOR MONITORING THE CONCENTRATION THEREOF

FIELD OF THE INVENTION

This invention relates to water-treatment polymers and water-treatment compositions which are used in aqueous systems as particulate dispersants, scale inhibitors and corrosion inhibitors. The polymers are detectable in the visible light range upon contact with an appropriate photoactivator in appropriate amounts. The invention also relates to methods of monitoring the concentration of the water-treatment polymers in the aqueous systems.

BACKGROUND OF THE INVENTION

There are many aqueous industrial systems which require that various materials remain in a soluble, or suspended, or dispersed state. Typical aqueous systems include, for example, boiler water or steam generating systems, cooling water systems, gas scrubbing systems, pulp and paper mill systems, desalination systems, and downhole systems encountered during the production of gas, oil, and geothermal wells. In many cases, water contains (either naturally or by contamination) ingredients, such as inorganic salts, which can cause accumulation, deposition, and fouling problems. These salts are formed by the reaction of metal cations, such as calcium, magnesium or barium, with inorganic anions such as phosphate, carbonate and sulfate. These salts have low solubilities in water and as their concentration in solution increases, or as the pH or temperature of the water containing them increases, these salts tend to precipitate from solution, crystallize and form hard deposits of scale on surfaces. Scale formation is a problem in heat transfer devices, boilers, secondary oil recovery wells, automatic dish washers and on substrates washed with such hard waters.

Many cooling water systems constructed from carbon steel, including industrial cooling towers and heat exchangers, experience corrosion problems. Corrosion is combated by the addition of various inhibitors such as orthophosphate compounds and/or zinc compounds. The addition of phosphates, however, adds to the formation of highly insoluble phosphate salts such as calcium phosphate. The addition of zinc compounds can also lead to the precipitation of insoluble salts such as zinc hydroxide and zinc phosphate. Other inorganic particulates, such as mud, silt and clay, are commonly found in cooling water. These particulates tend to settle onto surfaces and thereby restrict water flow and heat transfer unless they are effectively dispersed.

The stabilization of aqueous systems containing scale forming salts and inorganic particulates involves one or a combination of mechanisms. Dispersion of the precipitated salt crystals is a stabilization mechanism believed to be the result of the adsorption of the inhibitor onto precipitated crystals. The adsorption of the inhibitor can also be used to stabilize the system by facilitating the dispersion and subsequent removal of other suspended particulates, such as mud, silt and clay, and metals such as iron and zinc and their insoluble salts, from aqueous systems. Another stabilization mechanism involves the ability of the inhibitor to interfere with and distort the crystal structure of the scale, thereby making the scale less adherent to surfaces or other forming crystals or existing particulates.

Many different synthetic water-treatment polymers have been employed in a wide range of water-treatment applications as dispersants for particulate matter, inhibitors of mineral scale formation and deposition, and corrosion inhibitors. Polymers containing carboxylic acid and/or sulfonic acid functionality have been found to be particularly useful.

The water-treatment polymer is added to the aqueous system in a predetermined concentration which is effective to inhibit the formation and deposition of mineral scale and to inhibit corrosion. Once the water-treatment polymers have been introduced into the aqueous systems, the concentration of the polymers in the aqueous system must be monitored by some means in order that the amount of polymer present in the system can be maintained at the predetermined concentration.

There have been many methods reported which have been used to monitor the concentration of the water-treatment polymers. For instance, inert fluorescent tracers such as 2-naphthalenesulfonic acid are used. The emissivity of a sample of water is compared to a standard solution of the fluorescent tracer. However, this method requires calibration of the emissivity instrumentation and compensation for "background fluorescence" which may be present in the system water or the water-treatment polymer.

Polymers "tagged" with chemically-bound ultraviolet/ visible light absorbing chromophores and fluorescent units have also been used to monitor and control the level of the water-treatment polymer. However, like the aforementioned method, emissivity testing, instrumentation and the calibration thereof, as well as background fluorescence, complicate the method.

Methods for the colorimetric determination of polycarboxylates and/or sulfonates in aqueous systems are also known. The method comprises adjusting the pH of a portion of the aqueous solution to a predetermined value. The exact pH value is dependent on whether one is testing for sulfonates or carboxylates. A metachromatic dye is added to the solution in amounts effective for interaction of the dye with the carboxylate groups or the sulfonate groups. The absorbance is then measured and compared to absorbencies of standard samples.

It would be desirable to develop a water-treatment polymer which is readily detectable at concentrations of less than 100 parts per million and to develop methods for detecting the water-treatment polymer at such concentrations. The polymers and methods should not involve the use of fluorescent tracers or dyes. Additionally, the performance of the water-treatment polymers themselves should not be adversely affected. The method should be able to be conducted in a relatively short period of time, preferably without the need for expensive and/or sensitive instrumentation or standardization methods. The method should be accurate in concentrations of less than 100 ppm.

SUMMARY OF THE INVENTION

The present invention is directed to water-treatment compositions which comprise water-soluble polymers which are used in aqueous systems as dispersants of particulate matter, and/or as inhibitors of mineral scale formation, and/or as inhibitors of mineral scale deposition, and/or as corrosion inhibitors and to methods for monitoring the concentration of those polymers in aqueous systems. The polymer comprises the polymerized residue of (a) at least one water-treatment monomer and (b) a photo-inert, latently-detectable moiety. The residue of the photo-inert, latently-detectable moiety is covalently attached to the polymer backbone. When the residue of the photo-inert moiety is contacted with an amount of a photoactivator which is effective to cause the residue of the photo-inert moiety to absorb within a wavelength ranging from 300 to 800 nanometers, the residue of the photo-inert moiety is detectable at concentrations of less than 100 parts per million. The methods according to the present invention will allow for the determination of the concentration of low levels, i.e., less than 100 ppm, of water-treatment polymer present in an aqueous system.

DETAILED DESCRIPTION OF THE INVENTION

"Water-treatment monomers", as used herein, refers to those monomers used in preparing polymers for use in the treatment of aqueous systems for problems associated with particulates and mineral scale, corrosion, emulsification, flocculation and other contaminations. Such monomers may be anionic, cationic, non-ionic or zwitterionic. Exemplary anionic monomers containing carboxylic and/or sulfonic functionality include, without limitation, (meth)acrylic acids and the alkali, alkaline earth or ammonium salts thereof, dicarboxylic acids such as maleic acid, fumaric acid and itaconic acid including the anhydrides and the alkali, alkaline earth or ammonium salts thereof, allyloxybenzenesulfonate monomers described in U.S. Pat. No. 4,892,898, in the name of Leighton et al., (meth)allylsulfonate and the alkali, alkaline earth or ammonium salts thereof, and vinyl sulfonic acid and the alkali, alkaline earth or ammonium salts thereof, acrylamido alkyl or aryl sulfonates such as 2-acrylamido-2-methyl propane sulfonic acid. Exemplary cationic monomers containing quaternary ammonium functionality include, without limitation, diallyldimethyl ammonium chloride (DADMAC), (meth) acrylamidopropyltrimethyl ammonium chloride ((M) APTAC), quaternary aminomethyl(meth)acrylamide (QAMAM), methacryloxyethyltrimethyl ammonium chloride (METAC), acryloxyethyltrimethyl ammonium chloride (AETAC), acrylamidoethylpropyl trimethyl ammonium chloride (AMPTAC), diethyldiallyl ammonium chloride (DEDAAC) and trimethylallyloxyethyl ammonium chloride (TAAC). Exemplary non-ionic monomers include, without limitation, alkyl substituted or unsubstituted (meth) acrylamides, alkyl esters of(meth)acrylic acids, hydroxyalkyl esters of (meth)acrylic acids, and amino alkyl esters of (meth)acrylic acids. Exemplary zwitterionic monomers include, without limitation, unsaturated carboxyl, sulfoxyl or sulfate-substituted amines, commonly referred to as betaines.

A polymerizable, photo-inert, latently-detectable moiety is combined with the water-treatment monomer(s) and the components are reacted such that the photo-inert, latently-detectable moiety is covalently attached to the polymer backbone upon polymerization. By photo-inert, it is meant that the latently-detectable moiety does not contain a chromophore which has a detectable absorbance in the visible region. By latently-detectable, it is meant that the photo-inert moiety will not be detectable in the visible light range until the moiety is contacted with an appropriate reagent which, when present in effective amounts, will react with the photo-inert moiety, thereby converting the moiety into a chemical species which strongly absorbs in the region of 300 to 800 nanometers, preferably 400 to 700 nanometers. Such an appropriate reagent is referred to herein as a photoactivator.

In preparing the polymerizable, photo-inert, latently-detectable moiety, a single, $\alpha,\beta$-ethylenically unsaturated moiety is covalently bonded to the photo-inert, latently-detectable moiety. The $\alpha,\beta$-ethylenically unsaturated moiety serves as the polymerizable functionality which allows copolymerization of the photo-inert, latently-detectable moiety and the water-treatment monomer. Accordingly, the $\alpha,\beta$-ethylenically unsaturated moiety may be any of those moieties which will copolymerize readily with a selected water-treatment monomer. Such unsaturated moieties include, for example, allyl, acrylate, methacrylate and styrenic functionality. Preferred $\alpha,\beta$-ethylenically unsaturated moieties include acrylamide, methacrylamide and $\alpha$-methyl styryl moieties. Particularly preferred is 3-isopropenyl-$\alpha,\alpha$-dimethylbenzyl isocyanate.

The photo-inert, latently-detectable moiety and the photoactivator are selected such that contacting the two at predetermined concentrations and under appropriate conditions causes the photo-inert, latently-detectable moiety to absorb in the 300 to 800 nanometer range, preferably 450 to 800 nanometers, thereby allowing the "reacted" photo-inert moiety to be detectable when the water-treatment polymer is present in the aqueous system at low concentrations, i.e. less than 100 ppm. Preferably, the "reacted" moiety will be detectable where the water-treatment polymer is present at concentrations as low as 25 ppm and even more preferably at concentrations as low as 1 to 10 ppm.

The exact levels of use chosen for the latently-detectable moiety and the corresponding photoactivator will depend on such factors as the compositions of the latently-detectable moiety and the corresponding photoactivator themselves, the composition of the water-treatment polymer and/or water-treatment compositions as well as their levels of use, and the particular aqueous system being treated. For both economic and performance considerations, minimum amounts of the photo-inert, latently-detectable moiety are used. Maximum levels of use of the latently-detectable moiety are limited in one aspect by the dilution effect on the water-treatment properties of the water-treatment polymers. Preferably, the water-treatment polymers will comprise from about 0.5 to 5 mole percent of the photo-inert, latently detectable moiety, more preferably from about 1 to 4 mole percent.

Examples of photo-inert, latently-detectable moieties include, without limitation, (meth)acrolein and cinnamaldehyde. When one or the other are polymerized with a water-treatment monomer, for instance acrylic acid, a polymer having pendant aldehyde functionality is produced. One skilled in the art, once armed with the present specification, would be able to utilize known techniques for detecting aldehyde functionality. For instance, aldehyde functionality can be detected by a ferricyanide test. In this test, the aldehyde reduces the yellow ferricyanide to colorless ferrocyanide and, therefore, the more reducing aldehyde present, the less yellow ferricyanide there is to measure. The technique can be made more sensitive by the further addition of a ferric ion solution which yields a Prussian blue color. Absorbance is measured at 690 nanometers and is proportional to the concentration of the aldehyde groups. Another example of a photo-inert, latently-detectable moiety which could be appended to a polymer backbone are phenol groups. Color could be developed from these functional entities upon the addition of nitric acid and sulfuric acid, since the resultant nitrophenols typically have a red coloration.

Another polymerizable, photo-inert, latently-detectable moiety according to the present invention is a polymerizable saccharide moiety. Generally, the saccharide moiety may be composed of glycosyl units connected by glycosidic linkages. They can be linear or branched, and they may be composed of a single type of glycosyl unit or they may be composed of two or more different types of glycosyl units. Exemplary saccharides according to the present invention include, without limitation, starches, hydrolyzed starches, lactose, maltose, maltodextrins, corn syrup solids, cellulose, hydrolyzed cellulose, dextran, hydrolyzed dextran, guar gum, hydrolyzed guar gum, locust bean gum and hydrolyzed locust bean gum. Such starches include, for example, corn, potato, tapioca and rice starches.

The polymerizable saccharide moieties may be prepared by a number of methods. For instance, reductive amination, with or without a solvent, may be used to prepare the polymerizable saccharide moieties. Additionally, the polymerizable saccharide moieties may be prepared by, for example, condensation of 1-amino-1-deoxy-D-maltitol with methacrylic anhydride to give the corresponding methacrylamide, or treatment of maltonolactone with p-vinylbenzylamine to give a N-p-vinylbenzylmaltonamide, or by lipase catalyzed transesterification of an active ester of acylic acid, such as vinyl acrylate, with saccharides or saccharide derivatives.

More specifically, the saccharide monomer is represented by Structure III:

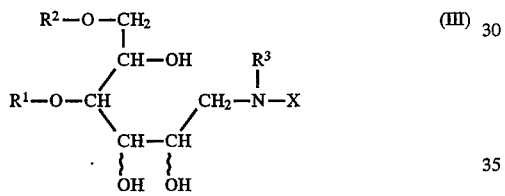

wherein $R^1$, $R^2$ and $R^3$ are as defined herein below and X is the residue of the α,β-ethylenically unsaturated moiety. Preferably, X is the residue of a moiety selected from the group consisting of acrylamide, methacrylamide and α-methyl styryl moieties.

The preferred methods used to prepare the polymerizable saccharide moieties, reductive amination, preferably utilize only water as the reaction solvent and preferably are free of a cosolvent. In one embodiment, the process comprises mixing together, in water and in the absence of a cosolvent, a saccharide moiety of structure (I) with an amine of the formula $R^3NH_2$, where $R^3$ may be $C_1$–$C_{18}$ alkyl, H or $NH_2$. The admixture of the saccharide and the amine are contacted with pressurized hydrogen, in the presence of a Group VIIIB metal catalyst and under conditions effective to produce an amino saccharide of structure (II). The amino saccharide is reacted with the α,β-ethylenically unsaturated moiety to form a saccharide monomer of structure (III).

As used herein, the term "saccharide" is intended to include oligosaccharides and polysaccharides, as those terms are known to one skilled in the art. The terms "saccharide monomers" and "polymerizable saccharide moieties" are used interchangeably herein.

Preferably, the polymerizable saccharide moieties of the present invention are prepared by:

(a) mixing together, in water and in the absence of a cosolvent, (i) a saccharide of structure (I);

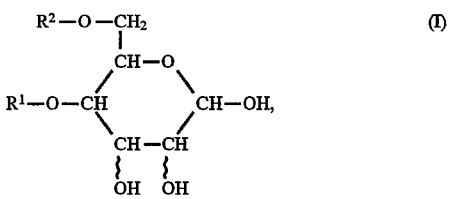

wherein, $R^1$ is H or is represented by structure I(a)

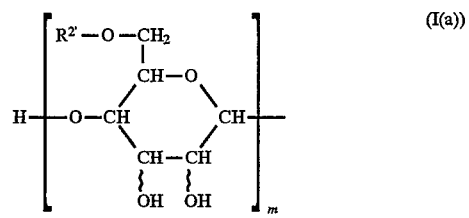

$R^2$ is H, or is represented by structure I(a) or structure I(b)

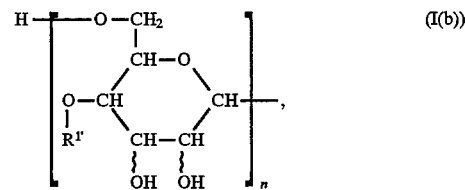

wherein $R^1$ is H or is represented by structure I(a),
$R^2$ is H or is represented by structure I(a) or structure I(b), and wherein $R^1$ and $R^2$ are not both H and the average of ($\Sigma m + \Sigma n$) is greater than or equal to 1, and (ii) an amine selected from the group consisting of $R^3NH_2$, where $R^3$ is selected from the group consisting of a $C_1$–$C_{18}$ alkyl group, H or $NH_2$, thereby producing an aqueous admixture of the saccharide and the amine, (b) contacting the aqueous admixture of the saccharide and the amine with hydrogen, under pressure, in the presence of a Group VIIIB metal catalyst and under conditions effective to produce an amino saccharide of structure (II);

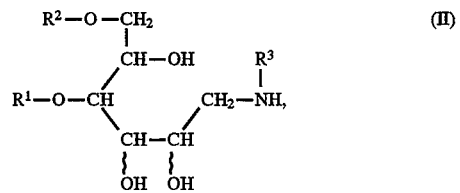

wherein $R^1$, $R^2$, $R^3$, $R^{4'}$, $R^{2'}$, m and n are as above, (c) adding the α,β-ethylenically unsaturated moiety to the amino saccharide; and (d) mixing the amino saccharide and the α,β-ethylenically unsaturated moiety under conditions effective to produce a saccharide monomer of structure (III), wherein $R^1$, $R^2$, $R^3$, $R^{1'}$, $R^{2'}$, X, m and n are as above and wherein the catalyst and excess amine are removed from the reaction.

In preferred embodiments, the methods of preparing the saccharide monomers exclude the use of a cosolvent with the water throughout the process for preparing the saccharide monomers. Cosolvent, as used herein, is intended to include organic solvents, such as alcohols, ketones, and polar aprotic solvents such as dimethyl sulfoxide, dimethyl formamide and pyridine. Cosolvent, as used herein, is also intended to include excess amine utilized in the process to the extent that the amine is present in amounts effective to function as a solvent in the process.

In forming the admixture of the saccharide of structure (I) and the amine, the saccharide and the amine are mixed together in water and in the absence of a cosolvent until an admixture thereof is formed. In preferred embodiments, the saccharide is added to water and blended until the saccharide is either dissolved in the water or homogeneously dispersed in the water. The saccharide/water mixture is added to the amine and blended, preferably at temperatures less than about 10° C., for a time effective to form an admixture of the saccharide and the amine, typically at least about one hour.

Preferred saccharide moieties used to prepare the polymers of the present invention are represented by structure (I), where $R^1$ and $R^2$ are as set forth herein above. In particularly preferred embodiments, the polysaccharide is a starch represented by structure (I) where $R_1$ is represented by structure I(a) and $R^2$ is represented by structure I(a) or is H. The amine used in the present invention is selected from the group consisting of $R^3NH_2$, where $R^3$ may be a $C_1$-$C_{18}$ alkyl group, H or $NH_2$. Preferably, $R^3$ is a $C_1$-$C_3$ alkyl group. More preferably, the amine is methylamine. Preferred $\alpha,\beta$-ethylenically unsaturated moieties comprise an $\alpha$-methyl styryl moiety, most preferably, 3-isopropenyl-$\alpha$, $\alpha$-dimethylbenzyl isocyanate.

In the preferred embodiments, the admixture of the saccharide and the amine are contacted with hydrogen, under pressure and in the presence of a Group VIIIB metal catalyst, for a period of time effective to produce an amino saccharide of structure (II). Preferably, the admixture of the saccharide and the amine is placed in a reactor with the Group VIIIB metal catalyst and the contents brought to a temperature adequate to facilitate the formation of the amino saccharide. Preferably, the temperature is from 10° C. to 100° C., more preferably from 40° C. to 60° C. The metal catalyst utilized may comprise any of the Group VIII metals, with nickel, palladium, platinum and ruthenium being preferred. Particularly preferred catalysts are Raney nickel catalyst and supported nickel catalysts such as those available from United Catalysts Inc., Louisville, Ky., under the trade name G-49B. The reactor is purged with nitrogen or a comparable inert gas and pressurized with hydrogen. The pressure will be effective to facilitate the reaction between the saccharide and the amine. Generally, the higher the pressure, the quicker is the reaction. Preferably the pressure will be at least about 100 psi, more preferably at least about 700 psi. The contents of the reactor are mixed until the reaction is substantially completed. Typically, the contents are mixed for about 8 to 20 hours, preferably about 12 hours. The temperatures and pressures noted above are not intended to limit the scope of the claims appended hereto. As one skilled in the art will recognize, once armed with the present specification, the conditions of temperature and pressure may be selected such that the reaction rate and product yield may be optimized.

After the amino saccharide has been formed, the catalyst must be removed therefrom. While one skilled in the art will appreciate that there are various means to remove the catalyst, in preferred embodiments, the catalyst is removed via filtration. The amino saccharide may be further concentrated to a solid, if so desired, and redissolved in water prior to forming the saccharide monomers of the present invention. Preferably, after the catalyst is removed, 3-isopropenyl-$\alpha$,$\alpha$-dimethylbenzyl isocyanate is added to the amino saccharide and the two are mixed under conditions effective to produce the saccharide monomer.

In preferred embodiments, a stoichiometric excess of the amine is mixed with the saccharide to facilitate the reaction of the saccharide with the amine. Without intending to be limited by the following, as the amino saccharide is formed, a less preferred reaction between the amino saccharide and the saccharide is believed to take place. A stoichiometric excess of the amine is used to facilitate the preferential reaction between the saccharide and the amine. It is preferred that the excess amount of amine used in the process be minimized, as any excess amine must be removed prior to the reaction of the amino saccharide with the 3-isopropenyl-$\alpha$,$\alpha$-dimethylbenzyl isocyanate. In addition, the amine is not used in excess amounts to the extent that it will function as a solvent in the process. Preferably, the saccharide and amine are used at molar ratios of 1:1 to 1:2, preferably from 1:1 to 1:1.5.

The amino saccharide and the 3-isopropenyl-$\alpha$,$\alpha$-dimethylbenzyl isocyanate are preferably combined in molar ratios ranging from about 0.8:1 to about 1.2:1, respectively. In more preferred embodiments, the amino saccharide and the 3-isopropenyl-$\alpha$,$\alpha$-dimethylbenzyl isocyanate are combined in equimolar amounts.

The preferred saccharide monomers of the present invention are unique in that they will copolymerize readily with acrylic monomers such as (meth)acrylates and sulfonic monomers such as sodium methallyl sulfonate, yet will not homopolymerize due to the nature of the $\alpha$-methyl styryl moiety. This property of the saccharide monomers is particularly advantageous where selective copolymerization with the respective comonomer is desired without the formation of saccharide homopolymers. This not only provides homogeneous copolymers, but also allows one to minimize the amount of saccharide monomer required to prepare the particular copolymer which contains the saccharide monomers. As the saccharide monomers are monofunctional, i.e., they contain a single, polymerizable $\alpha$-methyl styryl moiety, crosslinking and gelling are avoided during polymerization.

The polymers of the present invention may be prepared by any number of conventional means well known to those skilled in the art including, for instance, such techniques as bulk, emulsion, suspension, precipitation, or preferably solution polymerization.

The polymers are preferably prepared in an aqueous medium in the presence of any catalyst capable of liberating free radicals under the reaction conditions employed. Suitable catalysts include peroxides such as benzoyl peroxide, azo compounds such as azobisisobutyronitrile, and salts of peracids (e.g., sodium or potassium persulfate). Redox systems employing, for example, t-butyl hydroperoxide may also be employed. The molecular weight of the polymers may be controlled by various compounds used in the art including for example chain transfer agents such as mercaptans, ferric and cupric salts, bisulfites, and lower alcohols (preferably isopropanol).

Once prepared, the water-treatment polymers may be added to the aqueous systems neat, although the polymers preferably are incorporated into a water-treatment composition comprising the water-treatment polymer and additional water-treatment chemicals. The water treatment chemicals vary depending on end use application. For cooling tower applications these water treatment chemicals include, without limitation, phosphonates, phosphates and phosphoric acid anhydrides, biocides, corrosion inhibitors such as zinc and molybdenum salts and oxides and azoles, and alkali metal and alkaline earth hydroxides. For boiler water applications these water treatment chemicals include, without limitation, oxygen scavengers, such as sodium metabisulfite and hydrazine, phosphates and phosphoric acid anhydrides, chelants, such as EDTA, NTA or DTPA, and amines such as ammonia, morpholine and cyclohexylamine. For oil field applications these water treatment chemicals include, without limitation, amides, imidazolines, amidoamines, phosphonates, freezing point depressants such as methyl alcohol, ethylene glycol and propylene glycol, biocides, polyethylene glycols, polypropylene glycols and fatty acids. For waste water treatment these water treatment chemicals include, without limitation, coagulants, such as alum, poly(aluminum chloride) and iron salts, surfactants, biocides, and alkali metal and alkaline earth hydroxides. The level of the inventive water-treatment polymer utilized in the water-treatment compositions will be determined by the treatment level desired for the particular aqueous system to be treated. The water-treatment compositions generally contain from about 4 to 25 weight percent of the water-treatment polymer, based on the total weight of the water-treatment composition. Exemplary water treatment compositions are set forth below.

| Formulation 1 | Formulation 2 |
| --- | --- |
| 11.3% Polymer (40% active) | 11.3% Polymer (40% active) |
| 47.7% Water | 59.6% Water |
| 4.2% Hydroxyethylidene diphosphonic acid (HEDP) | 4.2% HEDP |
| 10.3% NaOH | 18.4% Potassium pyrophosphate |
| 24.5% Sodium Molybdate | 7.2% NaOH |
| 2.0% Tolyltriazole | 2.0% Tolyltriazole |
| pH 13.0 | pH 12.6 |

| Formulation 3 | Formulation 4 |
| --- | --- |
| 22.6% Polymer (40% active) | 11.3% Polymer (40% active) |
| 51.1% Water | 59.0% Water |
| 8.3% HEDP | 4.2% HEDP |
| 14.0% NaOH | 19.3% NaOH |
| 4.0% Tolyltriazole | 2.0% Tolyltriazole |
| pH 12.5 | 4.2% ZnCl2 |
| | pH 13.2 |

In methods utilized to detect and monitor the concentration of the water-treatment polymer present in the aqueous systems, a sample of a predetermined volume is extracted from the aqueous system which contains the water-treatment polymers of the present invention. In water-treatment systems, there generally is a large aqueous volume from which to extract a sample and it may be desirable to take, for example, a 100 ml sample. Although not required to practice the method of the present invention, the sample could then be concentrated to, for example, 10 ml. One skilled in the art will recognize that any means of concentrating the sample may be utilized. Concentration of the sample may be accomplished by evaporation, for instance over a hot plate. Another method of concentrating the sample is by solid phase extraction (SPE). In this way, the technique would be more sensitive by an amount corresponding to the degree of concentration of the sample.

In using the SPE method of concentration, a proper size SPE tube is selected based on the sample volume, degree of contamination of the sample, complexity of the sample matrix, quantity of compounds of interest, solvent strength of the sample matrix and the strength of sorbent/analyte interaction. The tube is then conditioned to activate the packing contained within the tube. Conditioning solvents depend on the tube packing and application. The sample is transferred to the tube, preferably using a volumetric pipette or micropipette. The sample is passed through the extraction tube, using either vacuum or positive pressure. The packing is washed with appropriate solvent to remove materials which are not of interest or are unwanted. The water-treatment polymer is eluted from the extraction tube by rinsing the packing with a solution that removes the water-treatment polymer.

The sample, concentrated or unconcentrated, is contacted with an appropriate photoactivator at predetermined concentrations and under conditions which cause the photo-inert, latently-detectable moiety on the polymer backbone to absorb in the 300 to 800 nanometer range. The exact photoactivator, the level of use and conditions under which the two components are contacted depend upon the particular photo-inert, latently-detectable moiety being detected.

The concentration of the water-treatment polymer in the sample is determined by comparison to a set of standards. The concentration may be determined using a UV/VIS spectrophotomer. In this case, the absorbance of the sample is measured and compared to established absorbance standards. Alternately, the determination may be made by visual observation. In this case, an established set of standards is prepared by reacting the particular photo-inert, latently-detectable moiety at various concentrations with the photoactivator. The standards thus produced may be freshly prepared, in which a fresh set of standards of increasing intensity is produced. A color chart may also be produced representing a set of standards of increasing color intensity. The color of the test sample simply is compared to the colorimetric standards to determine the concentration thereof.

The following examples are in no way meant to limit the breadth of the claims appended hereto but are submitted merely to present preferred embodiments of the present invention.

Preparation of Polymer

A. Reductive Amination

α-D-lactose monohydrate (100 g, 0.28 mole) was dissolved in water (150 ml) with the aid of stirring and heating. The solution was cooled to room temperature and then added over two hours to a solution of methylamine (40% w/w in water, 43 g, 0.55 mole) in water (50 ml) while stirring under nitrogen gas and held at 0° to 10° C. The resultant mixture was stirred for a further one hour and then poured into a pressure vessel and United Nickel Catalyst G49-B (10 g) was added. The pressure vessel was then heated at 55° C. under an atmosphere of 700 p.s.i. hydrogen gas for 24 hours. After this time, the reaction vessel was depressurized and the catalyst was removed by filtration first through filter paper and then through Celite. A small sample of the flitrate was evaporated to dryness on a vacuum pump and then titrated versus dilute hydrochloric acid to determine that the reaction was complete. The rest of the sample was evaporated to low volume to ensure removal of excess methylamine and then it was treated directly with 3-isopropenyl-α,α-dimethylbenzyl isocyanate as detailed below.

B. Urea Formation

To a solution of N-methyl-D-lactamine (95 g, 0.27 mole) in water (350 ml) was added 3-isopropenyl-α,α-dimethylbenzyl isocyanate (54 g, 0.27 mole) and the resultant two phase mixture was vigorously stirred for ten hours. The course of the reaction was monitored by observance of the disappearance of the isocyanate peak at ~2250 cm$^{-1}$ in an infra-red spectrum obtained of the reaction mixture. A small amount of an off-white precipitate was formed and was removed by filtration. Unreacted aminosaccharide (<5%), as determined by titration of the reaction mixture versus dilute hydrochloric acid, was removed by the addition of Amberlite IR-120 (plus) ion exchange resin and stirring for four hours. The resin was then filtered and the solution was freeze dried to yield a white solid (143 g, 96%) whose NMR data was consistent with the structure proposed. The monomer so prepared was designated Monomer A.

A second polymerizable saccharide monomer was prepared as above except that a maltodextrin with a dextrose equivalence of 10 (DE=10) was used in place of the α-D-lactose monohydrate. The monomer was designated Monomer B.

A third polymerizable saccharide monomer was prepared as above except that a corn syrup solids with a dextrose equivalence of 24 (DE=24) was used in place of the α-D-lactose monohydrate. The monomer was designated Monomer C.

C. Polymerization

To a reaction vessel is charged 135 grams of deionized water, 5 ppm of an iron salt and 52.2 grams of 2-propanol. In three separate feed containers are charged 1) acrylic acid (102.6 grams, 1.5 moles); 2) Monomer A (27.9 grams, 0.05 moles), 20 grams of 2-propanol and 30 grams of deionized water; and 3) Sodium persulfate (10.44 grams, 0.046 moles) and 50 grams of deionized water. The three feed containers are attached to the reaction vessel which is heated to approximately 85° C. The sodium persulfate solution is slowly added at such a rate to give uniform addition over 3.25 hours. After 0.25 hours, the acrylic acid and Monomer A solutions are added at such a rate to give uniform addition over 3 hours. The temperature is maintained at 85° C. over the entire reaction. The 2-propanol is distilled from the reaction mixture after all solutions have been added. The reaction is then neutralized with 75 grams of a 50% sodium hydroxide solution. The resulting polymer has a weight average molecular weight of 6461 and polydispersity of 2.06.

EXAMPLE 1

A series of standard solutions of Monomer A in distilled water was prepared at concentrations of 1000, 100, 10 and 1 ppm, respectively. Following the procedure of Dubois et al. (*Anal Chem. 1956, 28, 350*), 1 ml of the sugar solution, 1 ml of 5% phenol in water and 5 ml of concentrated sulfuric acid were mixed. This process generated heat and the mixtures were allowed to cool over 30 minutes. The absorbance was then measured over the wavelength range of 400 to 700 nm in standard 1 cm pathlength cells using a Perkin Elmer UV/VIS spectrophotomer. The absorbance maximum was observed at 488 nm. It was clear from this experiment that detection to tens of ppm was possible. A variation of this procedure is to use 2 ml of sugar solution, 0.05 to 0.1 ml 80% phenol in water and 5 ml of sulfuric acid. This change improved the sensitivity by a factor of approximately two.

A second series of standard solutions of Monomer B was prepared as above. The absorbance maximum was noted at 489 nm. It is immediately apparent from the results set forth in Table 1 that use of Monomer B improved the detection by a further factor of four. It was decided to move from the 1 cm pathlength cell to a 10 cm pathlength cell. Treatment of 6 ml of the sugar solution with 0.3 ml 80% phenol in water and 15 ml sulfuric acid gave a distinctive orange color, with an improvement in sensitivity by a factor of approximately 8. The last column of Table 1 shows the results of a repeat of the previous experiment on a different day using freshly prepared standard sugar solutions and a different bottle of sulfuric acid. The agreement between the two sets of data is very good, establishing the reproducibility of the procedure.

TABLE 1

| | Absorbance at 488 nm (Monomer A) or 489 nm (Monomer B) | | | | |
|---|---|---|---|---|---|
| Concentration of sugar/ppm | Monomer A + 5% Phenol in 1 cm cell | Monomer A + 80% Phenol in 1 cm cell | Monomer B + 80% Phenol in 1 cm cell | Monomer B + 80% Phenol in 10 cm cell | Monomer B + 80% Phenol in 10 cm cell |
| 1000 | 1.868 | | | | |
| 100 | 0.221 | 0.383 | 1.627 | | |
| 50 | | | 0.765 | | |
| 20 | | | 0.322 | 2.342 | |
| 10 | <0.05 | <0.05 | 0.194 | 1.121 | 1.343 |
| 8 | | | | | 0.954 |
| 6 | | | | | 0.756 |
| 5 | | | 0.072 | 0.592 | |
| 4 | | | | | 0.516 |
| 2 | | | | | 0.290 |
| 1 | <0.05 | | | 0.155 | 0.167 |
| 0.5 | | | | | 0.096 |
| 0.25 | | | | | <0.05 |

EXAMPLE 2

Following the same saccharide detection procedure employed above, colorimetric experiments were performed with Monomer C. As would be expected, the values for Monomer C follow Beers Law but are lower since this material has less sugar per unit of 3-isopropenyl-α,α-dimethylbenzyl isocyanate than the Monomer B analog. Monomer C can be easily detected at a level of 1 ppm, which is a very acceptable lower limit. Monomer C is detected at an intermediate level between the Monomers A and B and basically represents a balance between having the most detectable material and having a material with a low molecular weight so that in mass terms the amount of sugar incorporated in the polymer is not so excessive such that it detrimentally affects the water-treatment properties of the water-treatment polymers.

TABLE 2

Absorbance at 489 nm (Monomer B) or 487 nm (Monomer C)

| Concentration of sugar/ppm | Monomer B + 80% Phenol in 10 cm cell | Monomer C + 80% Phenol in 10 cm cell |
| --- | --- | --- |
| 50 | — | 3.029 |
| 20 | 2.342 | 1.565 |
| 10 | 1.121 | 0.738 |
| 5 | 0.592 | 0.389 |
| 1 | 0.155 | 0.069 |

EXAMPLE 3

Two copolymers of acrylic acid:Monomer A (95:5 mole percent) were prepared and identified as Polymers A1 and A2, respectively. The only difference between the two polymers was in the way the monomers were dissolved prior to polymerization. The first analytical technique performed was NMR to establish whether the incorporation of Monomers A1 and A2, respectively, into the polymer had been successful. $^1$H NMR clearly indicated that the polymer contained lactose and that the lactose was covalently bound through the α-methyl styryl unit. The $^{13}$C NMR spectra were also consistent with incorporation of Monomer A. Detection experiments with these polymer samples were performed in the same manner as for the monomers in Example 1 and the results are summarized in Table 3. The absorbance maximum was now observed at 485 nm in the polymer.

TABLE 3

Absorbance at 485 nm of Polymers A1 and A2

| Concentration of polymer/ppm | Polymer A1 + 0.15 ml 80% Phenol | Polymer A2 + 0.05 ml 80% Phenol | Polymer A2 + 0.05 ml 80% Phenol |
| --- | --- | --- | --- |
| 100 | 0.468 | 0.503 | |
| 80 | | | 0.408 |
| 60 | | | 0.308 |
| 50 | 0.336 | 0.266 | |
| 40 | | | 0.228 |
| 30 | | | 0.168 |
| 25 | 0.161 | 0.130 | |
| 20 | | | 0.127 |
| 15 | | | 0.083 |
| 10 | 0.068 | 0.059 | |
| 5 | 0.093 | <0.05 | |

As the results indicate, the values obtained for Polymers A1 and A2 agree very closely, indicating similar incorporation of the saccharide monomer into the polymer. As a different volume of phenol was added to Polymers A1 and A2, respectively, direct comparisons cannot be made. The lower limit for detection of these polymers was 5 to 10 ppm. The last two columns of data are for Polymer A2, but using different standard solutions prepared on different days. The agreement in the data is very good, again illustrating the reproducibility of the procedure.

EXAMPLE 4

Polymers B1 and B2 were prepared by polymerizing acrylic acid (98 mole percent) and Monomer B (2 mole percent). Polymers C1 and C2 were prepared by polymerizing acrylic acid (97 mole percent) and Monomer C (3 mole percent). The difference in each pair of samples was the process by which the polymer was prepared. Two comparative homopolymers of acrylic acid (without any incorporated saccharide) were also prepared.

Colorimetric detection experiments with the comparative samples of acrylic acid homopolymers and Polymers B1, B2, C1 and C2 were then performed. The first set of experiments were conducted on the comparative acrylic acid homopolymers to determine whether the absorbance readings at about 490 nm in the saccharide detection test were indeed from the saccharide moiety and not a function of the poly-acrylic acid backbone. As can be seen in Table 4, the level of absorbance measured for the poly-acrylate is only approximately 1% of the value measured for one of the saccharide-containing polymers, even with the blank at twice the concentration of the inventive sample. This experiment illustrates that the detection technique is selective to the saccharide component and is independent of the water-treatment monomer.

TABLE 4

Detection of Acrylic Acid Homopolymers

| Sample | Absorbance (487 nm) |
| --- | --- |
| 100 ppm polyacrylate | 0.0198 |
| 100 ppm polyacrylate | 0.0282 |
| 50 ppm Polymer B2 | 2.0613 |

EXAMPLE 5

To test the level of detection for each of the new polymer samples, a 10 ppm solution of each sample was prepared. The results of the standard colorimetric experiment are shown in Table 5. As expected, the absorbance values obtained for Polymer C1 and C2 are comparable, as are the values for Polymers B1 and B2. Three additional samples of Polymer B2, were prepared at concentrations of 1.5, 3.5 and 6 ppm. Detection of this polymer down to 3.5 ppm is acceptable, although the absorbance reading at 1.5 ppm is at the level of the background value.

TABLE 5

Detection of Acrylic Acid: Saccharide Copolymers

| Sample | Absorbance (487 nm) |
| --- | --- |
| 10 ppm Polymer B1 | 0.4244 |
| 10 ppm Polymer C1 | 0.1896 |
| 10 ppm Polymer C2 | 0.2379 |
| 10 ppm Polymer B2 | 0.4285 |
| 6 ppm Polymer B2 | 0.2443 |
| 3.5 ppm Polymer B2 | 0.1166 |
| 1.5 ppm Polymer B2 | 0.0133 |

EXAMPLE 6A

Five samples of Polymer B2 were prepared at concentrations of 10, 20, 30, 40 and 50 ppm, respectively. In addition, three samples of Polymer B2 at respective concentrations of 15, 35 and 60 ppm were prepared and designated as Unknowns 1, 2 and 3, respectively. After addition of phenol and sulfuric acid, the absorbance of each sample was measured at 487 nm using a UV/VIS spectrophotometer. The results are shown in Table 6A.

TABLE 6A

Spectrophotometer Detection of Polymer B2

| Concentration (ppm) | Absorbance (487 nm) |
|---|---|
| 50 | 2.0613 |
| 40 | 1.7163 |
| 30 | 1.2961 |
| 20 | 0.8123 |
| 10 | 0.4285 |
| 15 | 0.6238 |
| 35 | 1.4553 |
| 60 | 2.3523 |

EXAMPLE 6B

Unknown Samples 1 to 3 were submitted to a panel of 10 people in order to determine visually the concentration of the unknown samples compared to the set of standard solutions ranging from 10 to 50 ppm. The colorimetric standards were prepared by contacting the respective polymer samples with an effective amount of a photoactivator, which resulted in a series of standard solutions of increasing color intensity. The unknown samples were similarly contacted with the same photoactivator and under the same conditions which were used to prepare the standard color solutions. The panel compared the colors of the unknown solutions to those of the standards and estimated the concentration of the unknown samples by color observation. Results are set forth in Table 6B.

TABLE 6B

Visual Detection of Unknown Samples 1, 2 and 3

| Person | Estimated Concentration (ppm) | | |
|---|---|---|---|
|  | 1 | 2 | 3 |
| I | 15 | 30 | ≧50 |
| II | 10 to 20 | 30 | 50 |
| III | 10 to 20 | 20 to 30 | 40 to 50 |
| IV | 10 | 30 | ≧50 |
| V | 10 | ≦30 | 50 |
| VI | 15 | 40 | ≧50 |
| VII | 10 to 20 | 30 | 50 |
| VIII | 10 | 20–30 | 40 |
| IX | 10 | 30 | 50 |
| X | 15 | 30 | 50 |

Actual concentrations:
1–15 ppm
2–35 ppm
3–60 ppm

This experiment clearly illustrates that the concentrations of Unknowns 1, 2 and 3 were able to be estimated to within 5 to 10 ppm of their actual concentration. While the estimation of the concentration of Unknown 3 appears low in all cases, the set of standards given to the panel ranged only from 10 to 50 ppm and the panel was asked to estimate the concentrations of the unknowns based on the standards. Even though the standards only went to an upper limit of 50 ppm, three out of the ten people tested observed the concentration of Unknown 3 could be above 50 ppm.

EXAMPLE 7

Three solutions of Polymer B2 were prepared at respective concentrations of 1, 2.5 and 4 ppm. A 100 ml sample was taken using a measuring cylinder and this sample was added to a 150 ml beaker. The mixture was then stirred and heated on a hot plate until it had just boiled dry. A 10 ml portion of water was then added using a measuring cylinder. The three samples were labeled as Unknowns 4, 5 and 6, respectively, and submitted to a panel of five people for visual estimation of the concentrations as in Example 6B. The results are shown in Table 7. It is clear from these data that concentration of samples can lead to an accurate determination of the concentration of polymers in a given sample down to 1 ppm by a naked-eye observation and comparison to standards.

TABLE 7

Visual Detection of Unknown Samples 4, 5 and 6

| Person | Estimated Concentration/ppm | | |
|---|---|---|---|
|  | 4 | 5 | 6 |
| I | 1 | 2.5 | 3.5–4 |
| II | 1 | 2 | 4 |
| III | 1 | 3 | 4 |
| IV | 1 | 2 | 4 |
| V | 1 | 2 | 3.5 |

EXAMPLE 8

A series of solutions of Polymer B2 was prepared at concentrations of 1, 2, 3, 4 and 5 ppm, respectively. A solid phase extraction (SPE) tube which contained about 0.5 grams of an anion exchange packing material was conditioned with methanol (2 ml) and then water at pH about 7–10 (5 ml). A 100 ml sample of the polymer solution at pH 7 to 10 was passed through the packing material via a syringe. The packing material was washed with water at pH 7–10 (2×5 ml). The polymer was eluted from the packing material by passing water at pH 1 (2×2 ml) through the packing material. To the 4 ml sample thus collected were added 0.1 ml of 80% phenol solution, followed by 10 ml of sulfuric acid. The concentration of polymer in the original sample was determined by measuring the absorbance of the solution at 485 to 490 nm using a UV/VIS spectrophotometer. The results are set forth in Table 8.

TABLE 8

| Concentration (ppm) | Absorbance (487 nm) |
|---|---|
| 1 | 0.4795 |
| 2 | 0.8788 |
| 3 | 1.3367 |
| 4 | 1.6002 |
| 5 | 1.9700 |

EXAMPLE 9

A series of standard solutions at respective concentrations of 1, 2, 4, 6, 8 and 10 ppm was prepared for each of Polymers C3 and C4. Utilizing the SPE concentration protocol as discussed above, the absorbance of each solution was determined. Results are set forth in Table 9.

TABLE 9

| Polymer | Concentration (ppm) | Absorbance (487 nm) |
|---|---|---|
| Polymer C3 | 1 | 0.2280 |
|  | 2 | 0.3866 |

TABLE 9-continued

| Polymer | Concentration (ppm) | Absorbance (487 nm) |
|---|---|---|
| | 4 | 0.3227 |
| | 6 | 0.6401 |
| | 8 | 0.7818 |
| | 10 | 1.1684 |
| Polymer C4 | 1 | 0.3980 |
| | 2 | 0.5180 |
| | 4 | 0.6957 |
| | 6 | 0.7755 |
| | 8 | 1.0139 |
| | 10 | 1.1214 |

As the results indicate, there is a statistically significant correlation between absorbance and concentration down to 1 ppm.

Various polymers prepared as above were evaluated for scale inhibition properties, such as carbonate, phosphate and sulfate inhibition. The method used to determine phosphate inhibition is set forth below in detail. Similar methods for determining carbonate and sulfate inhibition were also performed using standard techniques such as those approved by the National Association of Corrosion Engineers. One skilled in the art of water treatment will appreciate that other methods which may be used to determine scale inhibition will yield similar results.

Phosphate Inhibition Test Protocol:
Solution "A":

Using sodium hydrogen phosphate and sodium tetraborate decahydrate, Solution A was prepared containing 20 mg/L of phosphate, and 98 mg/L of borate at a pH of from 8.0–9.5.

Solution "B":

Using calcium chloride dihydrate and ferrous ammonium sulfate, Solution B was prepared containing 400 mg/L of calcium and 4 mg/L of iron at a pH of from 3.5 to 7.0.

Antiscalant Preparation:

The total solids or activity for antiscalant(s) to be evaluated was determined. The weight of antiscalant necessary to provide a 1.000 g/L (1000 mg/L) solids/active solution was determined using the following formula:

(% solids or activity)/100%="X" "X"=decimal solids or decimal activity.

(1.000 g/L)/"X"=g/L antiscalant to yield a 1000 mg/L antiscalant solution

Sample Preparation:

Fifty (50) ml of Solution "B" was dispensed into a 125 ml Erlenmeyer flask using a Brinkman dispensette. Using a graduated pipet, the correct amount of antiscalant polymer solution was added to give the desired treatment level (i.e., 1 ml of 1000 mg/L antiscalant solution=10 mg/L in samples). Fifty (50) ml of Solution "A" was dispensed into the 125 ml Erlenmeyer flask using a Brinkman dispensette. Using a Brinkman dispensette, at least three blanks (samples containing no antiscalant treatment) were prepared by dispensing 50 ml of Solution "B" and 50 ml of Solution "A" to a 125 ml Edenmeyer flask.

The flasks were stoppered and placed in a water bath set at 70° C.±5° C. for 16 to 24 hours.

Sample Evaluation:

All of the flasks were removed from the water bath and allowed to cool to the touch. A vacuum apparatus was assembled using a 250 ml side-arm Edenmeyer flask, vacuum pump, moisture trap, and Gelman filter holder. The samples were filtered using 0.2 micron filter paper. The filtrate from the 250 ml side-arm Erlenmeyer flask was transferred into an unused 100 ml specimen cup. The samples were evaluated for phosphate inhibition using a HACH DR/3000 Spectrophotometer, following the procedure set forth in the operator's manual.

Calculate The Percent Inhibition For All Samples:

The percent inhibition for each treatment level is determined by using the following calculation.

$$\frac{S}{T} \times 100\% = \% \text{ Inhibition}$$

S=mg/L Phosphate for Sample
T=mg/L Total Phosphate added

EXAMPLE 10

Preliminary experiments with acrylate:saccharide copolymers indicated that they were inhibiting calcium scale formation. The findings are summarized in Table 10. Sample 900A is a control acrylic acid polymer which does not contain a saccharide monomer. All inventive polymers except Polymer C2 exhibited over 90% calcium carbonate stabilization at the 5 ppm treatment level.

TABLE 10

Evaluation of Acrylic Acid: Saccharide Copolymers as Antiscalants

| Polymer Sample | Treatment (mg/L) | Average % Inhibition |
|---|---|---|
| 900A | 1 | 39.2 |
| | 3 | 98.6 |
| | 5 | 98.6 |
| | 10 | 95.6 |
| Polymer B1 | 1 | 8.9 |
| | 3 | 64.3 |
| | 5 | 97.2 |
| | 10 | 95.6 |
| Polymer C1 | 1 | 9.9 |
| | 3 | 56.0 |
| | 5 | 93.3 |
| | 10 | 93.9 |
| Polymer C2 | 1 | 0.0 |
| | 3 | 40.9 |
| | 5 | 57.4 |
| | 10 | 96.3 |
| Polymer B2 | 1 | 4.4 |
| | 3 | 47.0 |
| | 5 | 96.0 |
| | 10 | 95.3 |

EXAMPLE 11

Polymer C3 was prepared utilizing acrylate and sulfonate water-treatment monomers (98 mole percent) and Monomer C (2 mole percent). The inventive polymer was compared with respect to calcium phosphate inhibition to an otherwise similar polymer which did not contain Monomer C. Results are set forth in Table 11.

TABLE 11

Calcium Phosphate Scale Inhibition

| Polymer | Treatment/ppm | Average % Phosphate Inhibition |
|---|---|---|
| Polymer C3 minus saccharide monomer | 13 | 7.19 |
| | 15 | 8.96 |
| | 17 | 46.10 |

TABLE 11-continued

Calcium Phosphate Scale Inhibition

| Polymer | Treatment/ppm | Average % Phosphate Inhibition |
|---|---|---|
|  | 19 | 91.41 |
|  | 21 | 94.48 |
| Polymer C3 | 13 | 5.52 |
|  | 15 | 5.47 |
|  | 17 | 5.42 |
|  | 19 | 9.43 |
|  | 21 | 61.77 |

While the saccharide monomer does appear to contribute to a dilution affect with respect to calcium phosphate inhibition, inhibition of calcium phosphate by the inventive polymer is acceptable and may be improved yet further upon optimization of the overall water-treatment program.

EXAMPLE 12

Polymer C4 was prepared utilizing acrylic and maleic water-treatment monomers (99 mole percent) and Monomer C (1 mole percent). The inventive polymer was compared with respect to barium sulfate inhibition to an otherwise similar polymer which did not contain Monomer C. Results are set forth in Table 12.

TABLE 12

Barium Sulfate Scale Inhibition

| Polymer | Treatment | mg/L Barium A | mg/L Barium B | % Inhibition A | % Inhibition B | Avg. % Inhibition Average |
|---|---|---|---|---|---|---|
| Polymer | 2 | 23.42 | 33.30 | 31.04 | 46.36 | 38.70 |
| C4 | 4 | 54.72 | 55.31 | 79.57 | 80.48 | 80.03 |
| minus | 6 | 63.67 | 53.26 | 93.44 | 77.30 | 85.37 |
| saccharide | 8 | * | 62.44 | * | 91.54 | 96.54 |
| monomer |  |  |  |  |  |  |
| Polymer | 2 | 28.92 | 28.92 | 39.57 | 39.57 | 39.57 |
| C4 | 4 | 48.30 | 48.54 | 69.61 | 69.99 | 69.80 |
|  | 6 | 62.24 | 63.33 | 91.23 | 92.92 | 92.08 |
|  | 8 | 61.95 | 60.87 | 90.78 | 89.10 | 89.94 |

As the results indicate, Polymer C4 performed on a par with respect to barium sulfate when compared to the polymer which did not contain Monomer C.

We claim:

1. A method for monitoring the concentration of a water-treatment polymer in an aqueous system, the method comprising:

providing an aqueous sample of a predetermined volume from an aqueous system, which aqueous system contains a water-soluble, water-treatment polymer, said polymer comprising the polymerized residue of, at least one water-treatment monomer in amounts effective to provide the polymer with the capability of performing at least one of a water-treatment function selected from the group consisting of dispersing particulate matter, inhibiting the formation of mineral scale, inhibiting the deposition of mineral scale and inhibiting corrosion in an aqueous system; and a second monomer comprising a photo-inert, latently-detectable moiety, said moiety being present in amounts effective to be detected at polymer concentrations of less than 100 parts per million and within a wavelength range of from 300 to 800 nanometers when the photo-inert, latently-detectable moiety is contacted with an amount of a photoactivator which is effective to cause the photo-inert, latently detectable moiety to absorb within said wavelength range, contacting said aqueous sample with an amount of said photoactivator and under conditions which are effective to cause the photo-inert, latently-detectable moiety to absorb with the wavelength range of from 300 to 800 nanometers; and determining the concentration of the water-treatment polymer by comparing the absorbance of aqueous sample which has been contacted with said photoactivator to a set of standards which have been prepared utilizing said water-treatment polymer and said photoactivator.

2. The method according to claim 1 wherein the aqueous sample is concentrated prior to being contacted with said photoactivator.

3. The method according to claim 2 wherein the aqueous sample is concentrated by evaporation.

4. The method according to claim 2 wherein the aqueous sample is concentrated by solid phase extraction.

5. The method according to claim 1 wherein the concentration of the water-treatment polymer is determined by measuring the absorbance of the sample in the wavelength of 300 to 800 nanometers and comparing the absorbance of the aqueous sample which has been contacted with said photoactivator with the absorbance of the set of standards.

6. The method according to claim 1 wherein the photo-inert, latently detectable moiety is detectable within a wavelength range of from 400 to 700 nanometers when the photo-inert, latently-detectable moiety is contacted with the effective amount of the photoactivator and wherein the concentration of the water-treatment polymer is determined by visually comparing the color of the aqueous sample which has been contacted with said photoactivator with the color of the set of standards.

* * * * *